US00PP32740P3

(12) United States Plant Patent
Hoogkamp

(10) Patent No.: US PP32,740 P3
(45) Date of Patent: Jan. 5, 2021

(54) ***CURCUMA* PLANT NAMED 'CURALIROTI'**

(50) Latin Name: *Curcuma alismatifolia*
Varietal Denomination: Curaliroti

(71) Applicant: Timothy Johan Herman Hoogkamp, Doetinchem (NL)

(72) Inventor: Timothy Johan Herman Hoogkamp, Doetinchem (NL)

(73) Assignee: NUBILUS B.V., Naaldwijk (NL)

( * ) Notice: Subject to any disclaimer, the term of this patent is extended or adjusted under 35 U.S.C. 154(b) by 0 days.

(21) Appl. No.: 16/602,988

(22) Filed: Jan. 11, 2020

(65) Prior Publication Data

US 2020/0229338 P1 Jul. 16, 2020

Related U.S. Application Data

(60) Provisional application No. 62/918,088, filed on Jan. 12, 2019.

(51) Int. Cl.
*A01H 5/02* (2018.01)
*A01H 6/00* (2018.01)
*A01H 5/12* (2018.01)

(52) U.S. Cl.
USPC ..... Plt./421
CPC ..... *A01H 6/00* (2018.05); *A01H 5/12* (2013.01)

(58) Field of Classification Search
USPC ..... Plt./421
See application file for complete search history.

*Primary Examiner* — Susan McCormick Ewoldt
(74) *Attorney, Agent, or Firm* — C. A. Whealy

(57) ABSTRACT

A new and distinct cultivar of *Curcuma* plant named 'Curaliroti', characterized by its upright plant habit with outwardly arching leaves; moderately vigorous growth rate; freely clumping growth habit; dark green-colored leaves; freely flowering habit; and large dense inflorescences with light purple-colored upper flower bracts positioned above the foliar plane on strong and erect peduncles.

3 Drawing Sheets

Figure 1:
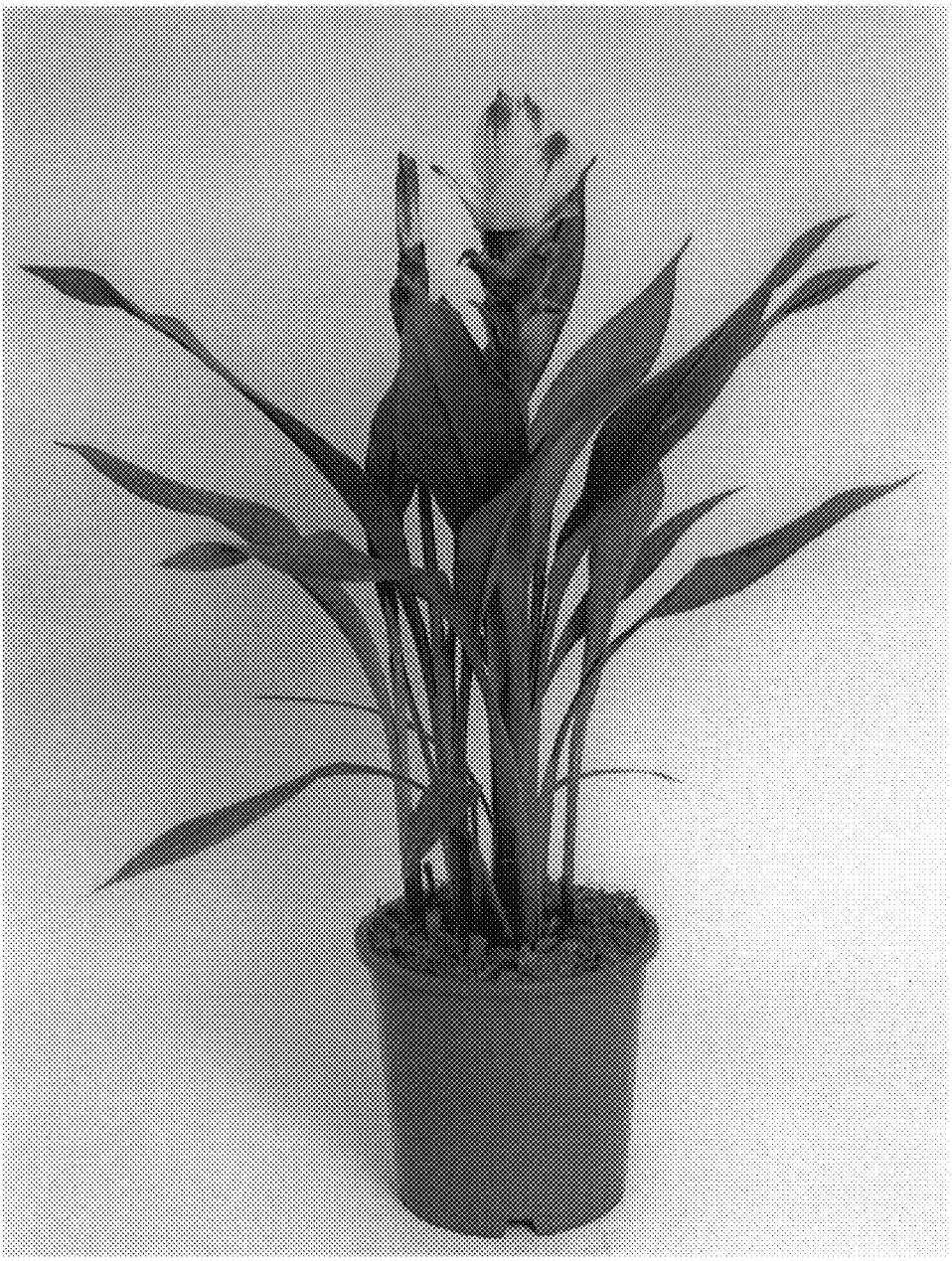

Botanical designation: *Curcuma alismatifolia.*
Cultivar denomination: 'CURALIROTI'.

BACKGROUND OF THE INVENTION

The present invention relates to a new and distinct cultivar of *Curcuma* plant, botanically known as *Curcuma alismatifolia* and hereinafter referred to by the name 'Curaliroti'.

The new *Curcuma* plant is a product of a controlled breeding program conducted by the Inventor in Naaldwijk, The Netherlands. The objective of the breeding program is to create new *Curcuma* plants that have uniform plant habit, good container performance and attractive inflorescence coloration.

The new *Curcuma* plant originated from a cross-pollination made by the Inventor in June, 2014 in Naaldwijk, The Netherlands of a proprietary selection of *Curcuma alismatifolia* identified as code number 20102602-023, not patented, as the female, or seed, parent with a proprietary selection of *Curcuma alismatifolia* identified as code number 20112725-024, not patented, as the male, or pollen, parent. The new *Curcuma* plant was discovered and selected by the Inventor as a single flowering plant within the progeny of the stated cross-pollination in a controlled greenhouse environment in Naaldwijk, The Netherlands in August, 2015.

Asexual reproduction of the new *Curcuma* plant by axillary meristem culture in a controlled environment in Naaldwijk, The Netherlands since June, 2016 has shown that the unique features of this new *Curcuma* plant are stable and reproduced true to type in successive generations of asexual reproduction.

SUMMARY OF THE INVENTION

Plants of the new *Curcuma* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Curaliroti'. These characteristics in combination distinguish 'Curaliroti' as a new and distinct *Curcuma* plant:

1. Upright plant habit with outwardly arching leaves.
2. Moderately vigorous growth rate.
3. Freely clumping growth habit.
4. Dark green-colored leaves.
5. Freely flowering habit.
6. Large dense inflorescences with light purple-colored upper flower bracts positioned above the foliar plane on strong and erect peduncles.

Plants of the new *Curcuma* differ from plants of the female parent selection in the following characteristics:

1. Plants of the new *Curcuma* grow faster than plants of the female parent selection.
2. Plants of the new *Curcuma* have light purple-colored upper flower bracts whereas plants of the female parent selection have darker purple-colored upper flower bracts.

Plants of the new *Curcuma* differ from plants of the male parent selection in the following characteristics:

1. Plants of the new *Curcuma* have longer postproduction longevity than plants of the male parent selection.
2. Plants of the new *Curcuma* have light purple-colored upper flower bracts whereas plants of the male parent selection have white-colored upper flower bracts.

Plants of the new *Curcuma* can also be compared to plants of *Curcuma alismatifolia* 'Curalimei', disclosed in U.S. Plant Pat. No. 25,124. In side-by-side comparisons plants of the new *Curcuma* differ from plants of 'Curalimei' in the following characteristics:

1. Plants of the new *Curcuma* grow faster than plants of 'Curalimei'.
2. Plants of the new *Curcuma* have light purple-colored upper flower bracts whereas plants of 'Curalimei' have darker purple-colored upper flower bracts.

BRIEF DESCRIPTION OF THE PHOTOGRAPHS

The accompanying photographs illustrate the overall appearance of the new *Curcuma* plant showing the colors as true as it is reasonably possible to obtain in colored reproductions of this type. Colors in the photographs may differ slightly from the color values cited in the detailed botanical description which accurately describe the colors of the new *Curcuma* plant.

The photograph on the first sheet (FIG. 1 of 3) is a side perspective view of a typical plant of 'Curaliroti' grown in a container and is the same photograph as filed in the U.S. Provisional Patent application Ser. No. 62/918,088.

Figure 2:
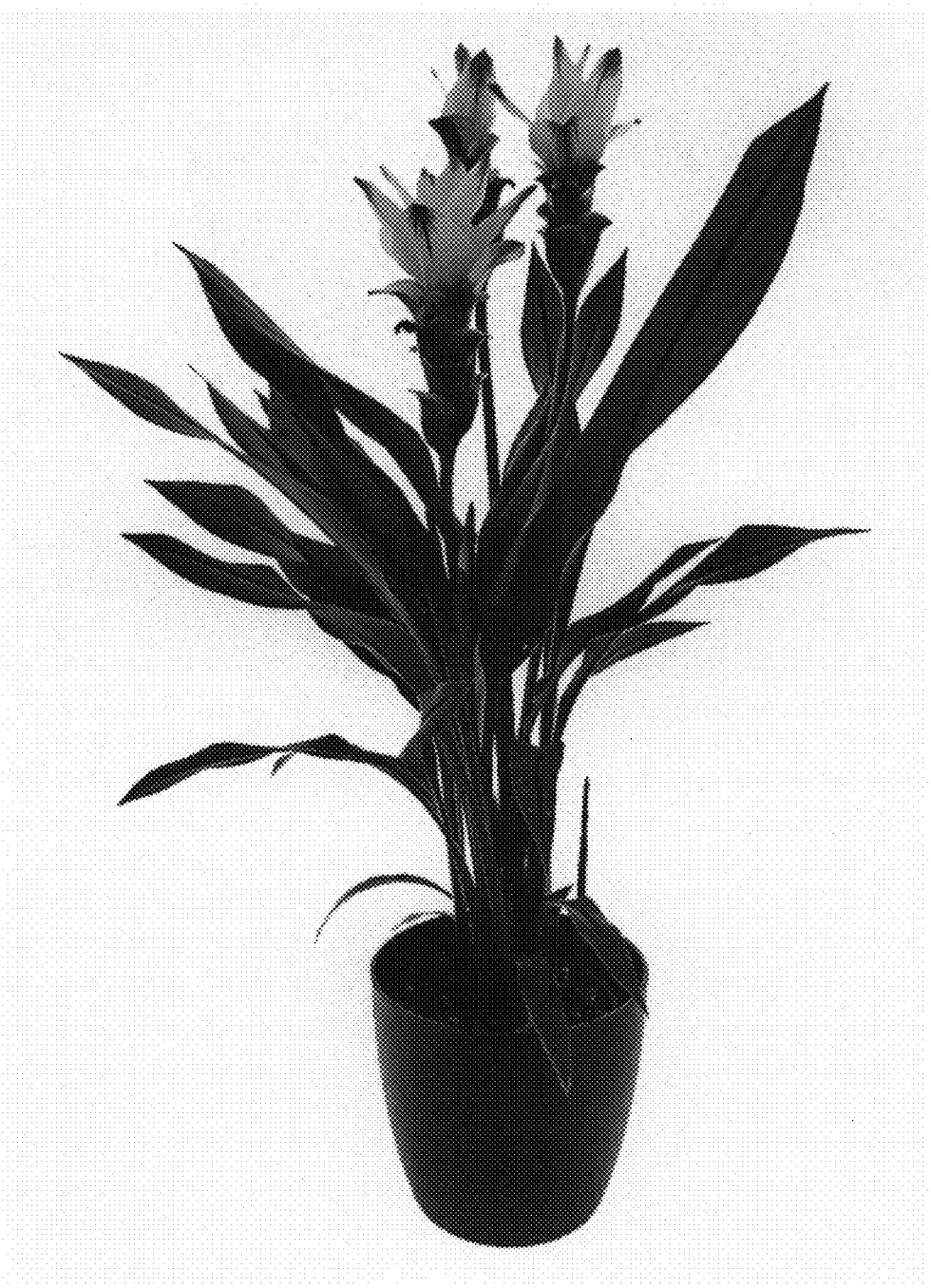

The photograph on the second sheet (FIG. 2 of 3) is a side perspective view of a typical plant of 'Curaliroti' grown in a container.

Figure 3:
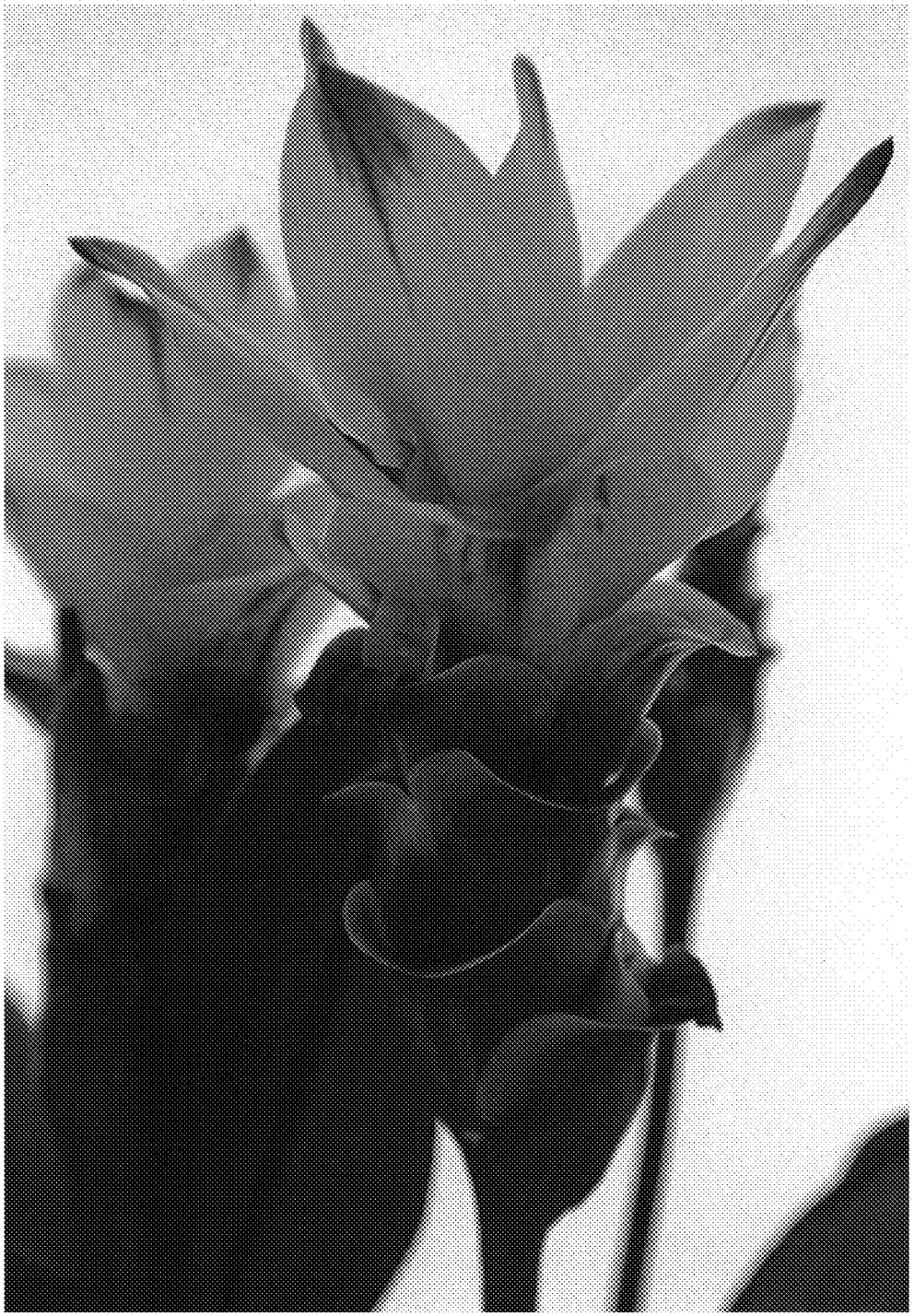

The photograph on the third sheet (FIG. 3 of 3) is a close-up view of typical inflorescences of 'Curaliroti'.

DETAILED BOTANICAL DESCRIPTION

The aforementioned photographs and following observations and measurements describe plants grown during the late spring in 13-cm containers in a glass-covered greenhouse in Naaldwijk, The Netherlands and under cultural practices typical of commercial *Curcuma* production. During the production of the plants, day temperatures ranged from 22° C. to 25° C., night temperatures ranged from 20° C. to 22° C. and light levels averaged 55 kilolux. Plants were 14 weeks old when the photographs and the detailed description were taken. In the following description, color references are made to The Royal Horticultural Society Colour Chart, 2015 Edition, except where general terms of ordinary dictionary significance are used.

Botanical classification: *Curcuma alismatifolia* 'Curaliroti'.

Parentage:

*Female, or seed, parent*.—Proprietary selection of *Curcuma alismatifolia* code number 20102602-023.

*Male, or pollen, parent*.—Proprietary selection of *Curcuma alismatifolia* code number 20112725-024.

Propagation:

*Type*.—By axillary bud meristem culture.

*Time to initiate roots*.—About ten days at temperatures about 23° C.

*Time to produce a rooted young plant*.—About 28 to 30 days at temperatures about 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately branching, medium density.

Plant description:

*Plant and growth habit*.—Upright plant habit with outwardly arching leaves; overall shape, broadly obovate; freely clumping habit with about seven basal shoots forming per plant; moderately vigorous growth habit and moderate growth rate.

*Plant height* (*soil level to top of foliar plane*).—About 44.4 cm.

*Plant height* (*soil level to top of floral plane*).—About 50.8 cm.

*Plant diameter*.—About 40.7 cm.

Leaf description:

*Leaf arrangement*.—Alternate; simple.

*Length, fully expanded*.—About 25.5 cm.

*Width, fully expanded*.—About 6.2 cm.

*Shape*.—Narrowly ovate.

*Apex*.—Long apiculate.

*Base*.—Attenuate, sheathing.

*Margin*.—Entire; unlobed and not undulate.

*Venation*.—Parallel.

*Aspect*.—Initially upright, then outwardly arching.

*Texture and luster, upper surface*.—Smooth, glabrous; non-rugose; matte to slightly glossy.

*Texture and luster, lower surface*.—Smooth, glabrous; non-rugose; matte.

*Color*.—Developing leaves, upper surface: Close to between 143C and 144A; main vein, close to between 175A and 177A. Developing leaves, lower surface: Close to between 143B and 143C; main vein, close to 138B. Fully expanded leaves, upper surface: Close to 137B and 138A; main vein, close to 178A; secondary veins, close to 137B. Fully expanded leaves, lower surface: Close to NN137C and 138A; main vein, close to 138B; secondary veins, close to NN137C.

*Leaf sheaths*.—Length: About 16 cm. Width: About 8 mm. Texture and luster, upper surface: Smooth, glabrous; moderately glossy to glossy. Texture and luster, lower surface: Smooth, glabrous; slightly glossy. Color, upper surface: Close to 144B. Color, lower surface: Close to 144C.

*Petioles*.—Length: About 21.4 cm. Width: About 7 mm by 8 mm. Strength: Strong. Texture and luster, upper surface: Smooth, glabrous; moderately glossy to glossy. Texture and luster, lower surface: Smooth, glabrous; slightly glossy. Color, upper surface: Close to between N138A and 144A. Color, lower surface: Close to 144B.

Inflorescence description:

*Arrangement*.—Upright terminal spike inflorescences developing directly from the basal shoots with showy upper flower bracts; typically each spike with about eleven clusters each with about five flowers; about 165 flowers buds and flowers developing per plant at one time.

*Time to flower*.—In The Netherlands, plants flower from summer into autumn; flowering continuous during this period; plants begin flowering about eleven weeks after planting.

*Flower longevity*.—Flowers last about three days on the plant; flowers persistent; plants maintain good substance for about 60 days.

*Fragrance*.—Faint; somewhat spicy.

*Flower buds*.—Length: About 2.2 cm. Diameter: About 6 mm. Shape: Oblanceolate. Texture and luster:

Smooth, glabrous; moderately glossy. Color: Proximally, close to 157C to 157D; distally, close to 85A.

*Inflorescence length*.—About 14.8 cm.

*Inflorescence diameter*.—About 9.4 cm.

*Flowers*.—Diameter: About 1.7 cm by 1.8 cm. Depth: About 3.3 cm. Flower throat diameter: About 1 cm. Flower tube length: About 1.3 cm. Flower tube diameter: About 4 mm. Shape and arrangement: Zygomorphic with three petals, conspicuous labellum and two lateral corolla lobes (staminodia), fused towards the base; gamosepalous calyx with three sepals.

*Labellum*.—Length: About 3.2 cm. Width: About 1.7 cm. Shape: Spatulate; fused at the base. Apex: Emarginate. Margins: Entire; slightly undulate. Texture and luster, upper surface: Smooth, glabrous; moderately velvety; matte. Texture and luster, lower surface: Smooth, glabrous; slightly glossy. Color: When opening and fully opened, upper surface: Close to N87A fading towards the center and base to close to 84A to 84B; central narrow stripe, close to 25B; venation, similar to lamina color; color becoming closer to N79A with development. When opening and fully opened, lower surface: Close to 83A fading towards the center and base to close to 85A; venation, similar to lamina color; color becoming closer to N79A with development.

*Lateral corolla lobes*.—Length: About 3.3 cm. Width: About 8 mm. Shape: Oblanceolate. Apex: Bluntly acute. Margins: Entire; not undulate. Texture and luster, upper surface: Smooth, glabrous; moderately velvety; matte. Texture and luster, lower surface: Smooth, glabrous; slightly glossy. Color: When opening and fully opened, upper surface: Close to NN155B; venation, similar to lamina colors; color becoming closer to N79A with development. When opening and fully opened, lower surface: Close to NN155B; venation, similar to lamina colors; color becoming closer to N79A with development.

*Petals*.—Length, dorsal petal: About 2.7 cm. Length, lateral petals: About 2.7 cm. Width, dorsal petal: About 8 mm. Width, lateral petals: About 7 mm. Shape, dorsal petal: Oblanceolate. Shape, lateral petals: Narrowly oblanceolate. Apex, dorsal petal: Narrowly obtuse. Apex, lateral petals: Bluntly acute. Base, dorsal and lateral petals: Proximal 50% of the petal length is fused into a tube. Margins, dorsal and lateral petals: Entire; not undulate. Texture and luster, dorsal and lateral petals, upper surface: Smooth, glabrous; moderately velvety; matte. Texture and luster, dorsal and lateral petals, lower surface: Smooth, glabrous; slightly glossy to moderately glossy. Texture, throat and tube: Smooth, glabrous. Color, dorsal and lateral petals: When opening and fully opened, upper surface: Close to NN155C fading towards the apex to close to 84D; venation, similar to lamina color; color does not change with development. When opening and fully opened, lower surface: Close to NN155C fading towards the apex to close to 84C; venation, similar to lamina color; color does not change with development. Color, flower throat: Close to NN155B; venation, close to NN155B. Color, flower tube: Close to NN155B; venation, close to NN155B.

*Calyx*.—Length: About 4 mm. Diameter: About 3 mm. Quantity of sepals and arrangement: Three in a single whorl; fused at the base. Sepal length: About 4 mm. Sepal width: About 2.5 mm. Sepal shape: Narrowly obovate. Sepal apex: Bluntly acute. Sepal base: Broadly cuneate. Sepal margin: Entire. Sepal texture and luster, upper and lower surfaces: Smooth, glabrous; moderately glossy. Sepal color: When opening and fully opened, upper surface: Close to NN155D. When opening and fully opened, lower surface: Close to NN155D.

*Upper flower bracts*.—Quantity: About eleven upper bracts per inflorescence. Length: About 7.3 cm. Width: About 4.6 cm. Shape: Elliptic to oblong; slightly concave. Apex: Broadly acute. Base: Cuneate. Margin: Entire; moderately undulate. Texture and luster, upper and lower surfaces: Smooth, glabrous; moderately glossy. Color: When opening and fully opened, upper surface: Close to 75C; towards the apex, close to 148B; blotched with close to 65A; towards the base, close to 145C to 145D; venation, similar to lamina; color does not change with development. When opening and fully opened, lower surface: Close to 76C; towards the apex, close to 146A to 146B; blotched with close to 65A; towards the base, close to 145B to 145C; venation, similar to lamina; color does not change with development.

*Lower flower bracts*.—Quantity: About eight lower bracts per inflorescence. Length: About 3.4 cm. Width: About 2.9 cm. Shape: Broadly obovate to inverted reniform; strongly concave. Apex: Obtuse. Base: Cuneate. Margin: Entire; undulate. Texture and luster, upper and lower surfaces: Smooth, glabrous; moderately glossy. Color: When opening and fully opened, upper surface: Close to 143B; towards the apex, close to 146A to 146B; distal blotch, close to 183A; venation, similar to lamina; color does not change with development. When opening and fully opened, lower surface: Close to 144A; venation, close to 147A; color does not change with development.

*Peduncles*.—Length: About 36 cm. Diameter: About 6 mm. Strength: Strong. Aspect: Mostly erect. Texture and luster: Smooth, glabrous; slightly glossy. Color: Close to 143A.

*Stamens*.—Quantity: Two per flower; fused. Filament length: About 2 mm. Filament color: Close to NN155D. Anther size: About 1.6 mm by 2 mm. Anther shape: Narrowly oblong. Anther color: Close to 155B; apex tinged with close to 86D. Pollen amount: Moderate. Pollen color: Close to 155C.

*Pistils*.—Quantity per flower: One. Pistil length: About 2.2 cm. Style length: About 2 cm. Style color: Close to NN155D. Stigma diameter: About 2 mm. Stigma shape: Cupped. Stigma color: Close to NN155D. Ovary color: Close to 157A.

*Seeds and fruits*.—To date, seed and fruit development have not been observed on plants of the new *Curcuma*.

Pathogen & pest resistance: To date, plants of the new *Curcuma* have not been observed to be resistant to pathogens or pests common to *Curcuma* plants.

Temperature tolerance: Plants of the new *Curcuma* have been observed to be tolerant to temperatures ranging from about 5° C. to about 40° C. and are suitable for USDA Hardiness Zones 10 to 12.

It is claimed:

1. A new and distinct *Curcuma* plant named 'Curaliroti' as illustrated and described.

* * * * *